(12) United States Patent
Fadell et al.

(10) Patent No.: US 9,562,819 B2
(45) Date of Patent: Feb. 7, 2017

(54) POLYMERIC REMOTE SEAL SYSTEM FOR SINGLE-USE CONTAINERS

(71) Applicant: Rosemount Inc., Chanhassen, MN (US)

(72) Inventors: Paul R. Fadell, Cypress, TX (US); Mark S. Schumacher, Minneapolis, MN (US); Joshua M. Price, Brenham, TX (US); Fred C. Sittler, Excelsior, MN (US)

(73) Assignee: Rosemount Inc, Chanhassen, MN (US)

( * ) Notice: Subject to any disclaimer, the term of this patent is extended or adjusted under 35 U.S.C. 154(b) by 8 days.

(21) Appl. No.: 14/788,069

(22) Filed: Jun. 30, 2015

(65) Prior Publication Data

US 2017/0003183 A1    Jan. 5, 2017

(51) Int. Cl.
*G08B 1/08* (2006.01)
*G01L 7/08* (2006.01)
*G08C 17/02* (2006.01)

(52) U.S. Cl.
CPC .......... *G01L 7/08* (2013.01); *G08C 17/02* (2013.01)

(58) Field of Classification Search
CPC .... G01L 7/08; G01L 19/0618; G01L 19/0007; B01L 3/505; G08C 17/02
USPC ................................................ 340/539.26
See application file for complete search history.

(56) References Cited

U.S. PATENT DOCUMENTS

| | | | |
|---|---|---|---|
| 7,258,017 B1 | 8/2007 | Hedtke | |
| 7,924,017 B2 | 4/2011 | Ammann et al. | |
| 8,123,397 B2 | 2/2012 | Baumfalk et al. | |
| 8,252,582 B2 | 8/2012 | Baumfalk et al. | |
| 2005/0163667 A1 | 7/2005 | Krause | |
| 2007/0151349 A1 | 7/2007 | Schumacher | |
| 2007/0272027 A1* | 11/2007 | Hedtke | G01L 19/0007 73/756 |
| 2012/0244609 A1 | 9/2012 | Selker et al. | |
| 2013/0145818 A1 | 6/2013 | Allgauer et al. | |
| 2015/0283279 A1* | 10/2015 | Lott | A61L 2/10 250/429 |

(Continued)

OTHER PUBLICATIONS

"90 | Wireless Monitoring Solution for Stackable Totes/Tanks", TankLink, a Division of Telular Corporation, available at www.TankLink.com, Copyright 2012 (2 pages).

(Continued)

*Primary Examiner* — Tai Nguyen
(74) *Attorney, Agent, or Firm* — Christopher R. Christenson; Kelly, Holt & Christenson, PLLC

(57) ABSTRACT

A polymeric remote seal system is provided for coupling a single-use container to a pressure measurement instrument. The polymeric remote seal system includes a process-side coupling, an instrument-side coupling and a fluidic coupling therebetween. The process-side coupling is configured to couple to the single-use container and is formed of a radiation sterilizable polymer. The process-side coupling has a process-side deflectable diaphragm that is configured to deflect in response to pressure within the single-use container. The instrument-side coupling is configured to couple to the pressure measurement instrument and is formed of a radiation sterilizable polymer. The instrument-side coupling is configured to fluidically convey fluid pressure to an isolation diaphragm of the pressure measurement instrument. Tubing fluidically couples the process-side coupling to the instrument-side coupling.

22 Claims, 12 Drawing Sheets

(56) References Cited

U.S. PATENT DOCUMENTS

2016/0091383 A1* 3/2016 Hoffman ............. G01L 19/0046
                                                                73/706

OTHER PUBLICATIONS

"90 | Wireless Monitoring Solution for Highly Corrosive Chemicals", TankLink, a Division of Telular Corporation, available at www.TankLink.com, Copyright 2013 (2 pages).
International Search Report and Written Opinion dated Oct. 20, 2016 for International Application No. PCT/US2016/038503.

* cited by examiner

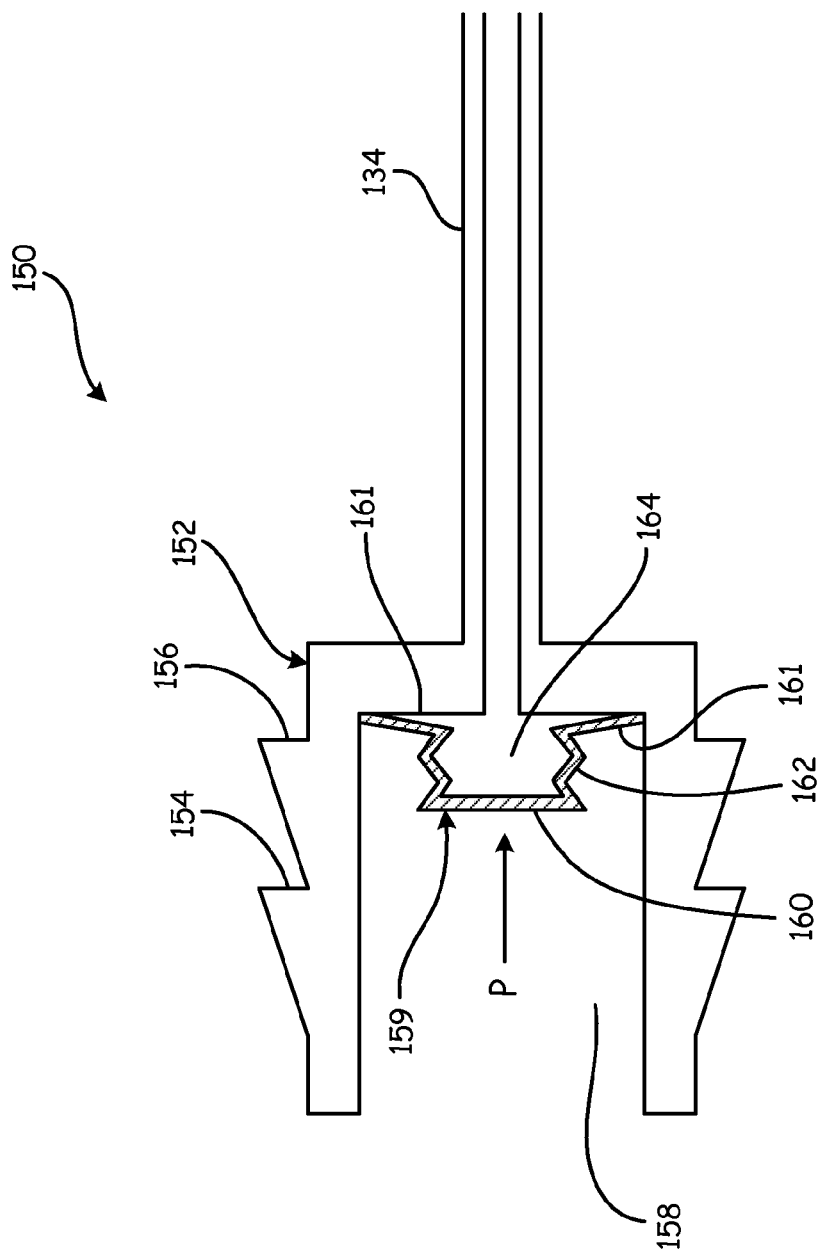

POLYMERIC REMOTE SEAL SYSTEM FOR SINGLE-USE CONTAINERS

BACKGROUND

Single-use containers, such as bioreactors, are useful for generating and supporting biological reactions for any number of purposes. Biological reactions can be susceptible to changes in temperature and/or pressure. Moreover, as the biological reaction progresses, the reaction itself may change various parameters within the bioreactor, such as the pressure. Accordingly, it may be important to monitor pressure or other variables of the biological reaction.

The life sciences industry is moving from large, capital-intensive facilities made of stainless steel with large clean-in-place (CIP) infrastructure to smaller facilities that use polymeric bags or containers functioning as bioreactors. The bioreactor bag is used once and then discarded. This single-use bioreactor technique significantly reduces the capital cost of the plant. For example, in existing facilities that use stainless steel CIP infrastructure, up to 90% of the cost of operating the facility may be due to the clean-in-place infrastructure, including very high end instrumentation designed to withstand a steam cleaning cycle. By moving to disposable, single-use bioreactor bags, the CIP portion of the capital can be eliminated and the facility can be more flexible and much smaller, which, in turn, allows the production of the smaller batches that are needed for more targeted drug therapies and other smaller-scale applications.

As pharmaceutical manufacturers change over from large stainless-steel process vessels to smaller-volume, pre-sterilized, disposable plastic bag systems, there is a need to measure pressure in these systems in order to control the growth environment and subsequent processes. Typically, pharmaceutical manufacturers and the life science industry in general, have used pressure sensors that are pre-sterilized and are disposed of after a single-use, which, in turn, has driven the life sciences industry to use inexpensive sensors. Such inexpensive sensors use relatively crude methods for fluid isolation, such as silicone gel. These methods can lead to inaccurate measurements, which are generally unacceptable to the life sciences industry for supporting the various biological reactions.

SUMMARY

A polymeric remote seal system is provided for coupling a single-use container to a pressure measurement instrument. The polymeric remote seal system includes a process-side coupling, an instrument-side coupling and a fluidic coupling therebetween. The process-side coupling is configured to couple to the single-use container and is formed of a radiation sterilizable polymer. The process-side coupling has a process-side deflectable diaphragm that is configured to deflect in response to pressure of the single-use container. The instrument-side coupling is configured to couple to the pressure measurement instrument and is formed of a radiation sterilizable polymer. The instrument-side coupling is configured to fluidically convey fluid pressure to an isolation diaphragm of the pressure measurement instrument. Tubing fluidically couples the process-side coupling to the instrument-side coupling.

BRIEF DESCRIPTION OF THE DRAWINGS

FIG. 2C is a partial cross-sectional view of a process-side connection of a remote seal system in accordance with another embodiment of the present invention.

DETAILED DESCRIPTION OF ILLUSTRATIVE EMBODIMENTS

Embodiments of the present invention generally leverage a remote seal system in order to couple pressure within single-use container such as a bioreactor to a high-precision pressure measuring instrument. Accordingly, the actual sensor that measures the pressure within the bioreaction vessel is disposed within the high-precision pressure measurement instrument. The remote seal system is formed of a polymeric material that is pre-sterilized, and, in some embodiments, physically coupled to a pre-sterilized single-use bioreactor. Accordingly, the bioreactor as well as the remote seal system itself are disposable. This allows the use of an accurate and precise reusable pressure transmitter but still provides the end user with a pre-sterilized connection to the bioreaction vessel. The field instrument-side and the process-side couplings will be described separately below. Embodiments of the present invention include any combination of the various process-side configurations with any of the various instrument-side configurations.

Figure 1:
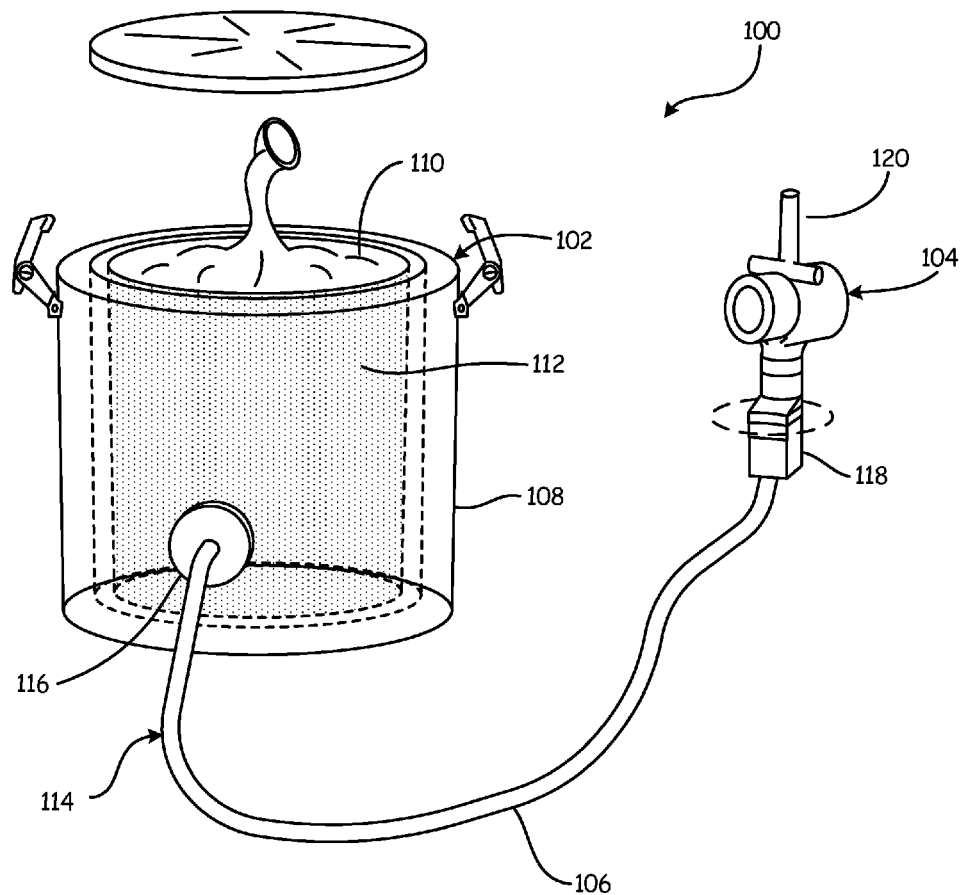
FIG. 1 is a diagrammatic view of single-use bioreactor employing a polymeric remote seal system in accordance with an embodiment of the present invention.

FIG. 1 is a diagrammatic view of a polymeric remote seal system used with a single-use bioreactor in accordance with an embodiment of the present invention. Bioreaction system 100 includes bioreactor 102 coupled to pressure measuring instrument 104 via fluidic coupling 106. Bioreactor 102 generally includes an outer support container 108 that has a wall that is relatively solid such that it forms a shell for single-use bioreaction bag 110 disposed therein. Outer shell 108 is generally matched to the dimensions and functionality of single-use bioreaction bag 110. However outer shell 108 is typically a reusable item. Single-use bioreactor bag 110 is generally a polymeric bag that is configured to support a biological reaction occurring within sample 112.

Polymeric remote seal system 114 couples the pressure within single-use bioreactor bag 110 to pressure measuring instrument 104. This coupling is a fluidic coupling such that pressure acting against a diaphragm disposed proximate process connection 116 generates movement of fluid within coupling 106 to cause associated movement at a diaphragm proximate instrument coupling 118. Such movement conveys the fluid pressure from bioreactor bag 110 to a pressure sensor within instrument 104 such that the pressure can be measured very accurately. Moreover, instrument 104 generally includes characterization and/or calibration information in order to compensate for variations in temperature and/or other environmental variables. Further, various embodiments of instrument 104 may also perform diagnostics relative to the device itself and/or the biological reaction in order to provide additional information instead of simply reporting the pressure within single-use bioreactor bag 110. Further still, instrument 104 may also be configured to convey the pressure information to one or more additional devices via a process communication loop or segment, such as that in accordance with the Highway Addressable Remote Transducer (HART®) protocol or the FOUNDATION™ Fieldbus protocol. Moreover, embodiments described herein may also include wirelessly transmitting such pressure information to any suitable device via antenna 120 in accordance with a wireless process communication protocol, such as IEC62591. In one embodiment, instrument 104 is a commercially-available hygienic pressure transmitter sold under the trade designation Model 3051 HT available from Emerson Process Management of Shakopee, Minn.

Figure 2A:
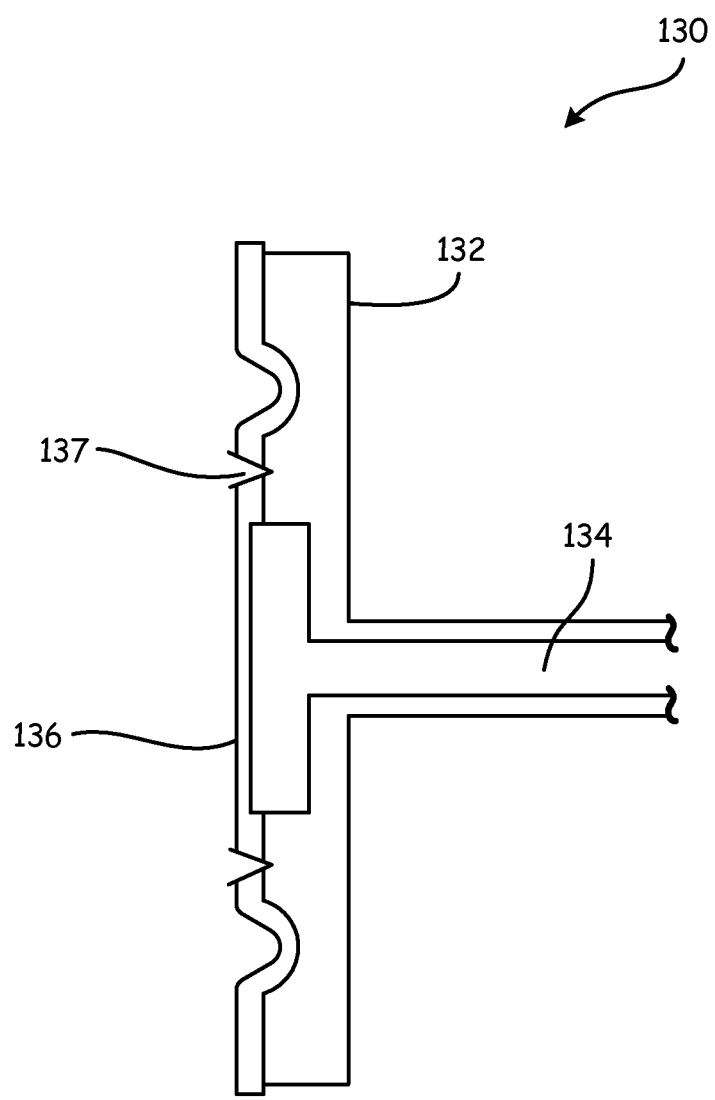
FIG. 2A is a partial cross-sectional view of a process-side connection of a remote seal system in accordance with an embodiment of the present invention.

FIG. 2A is a diagrammatic cross-sectional view of a process-side connection of a remote seal system to a single-use bioreactor in accordance with an embodiment of the present invention. Flange 130 includes flange body 132 that is fluidically coupled to tubing 134. A deformable isolation diaphragm 136 is coupled to flange body 132 in order to provide a fluid-tight seal. In one embodiment, flange body 132 is formed of a radiation-sterilizable polymer. One example of a radiation-sterilizable polymer is polyvinyl chloride. However any suitable radiation-sterilizable polymer can be used in accordance with embodiments of the present invention. In some embodiments, isolation diaphragm 136 is also formed of a radiation-sterilizable polymer of the same type as flange body 132. Diaphragm 136 may be coupled to flange body 132 in accordance with various techniques. For example, diaphragm 136 may be welded to flange body 132 at annular weld 137 using known welding techniques such as thermal, ultrasonic, or a combination thereof. Accordingly, the plastic wall of single-use bioreactor will bear against isolation diaphragm 136 and pressure within the bioreactor will deform diaphragm 136 thereby forcing fill fluid through tubing 134. The fill fluid can be any suitable fluid that is substantially incompressible at the pressures and temperatures of the application. The fill fluid may be silicone oil, water, or any other suitable fluid. As set forth above, this will generate associated movement of a similar diaphragm at the pressure measuring instrument, which deflection is then measured or otherwise characterized by a high-accuracy, precision pressure sensor within instrument 104.

Figure 2B:
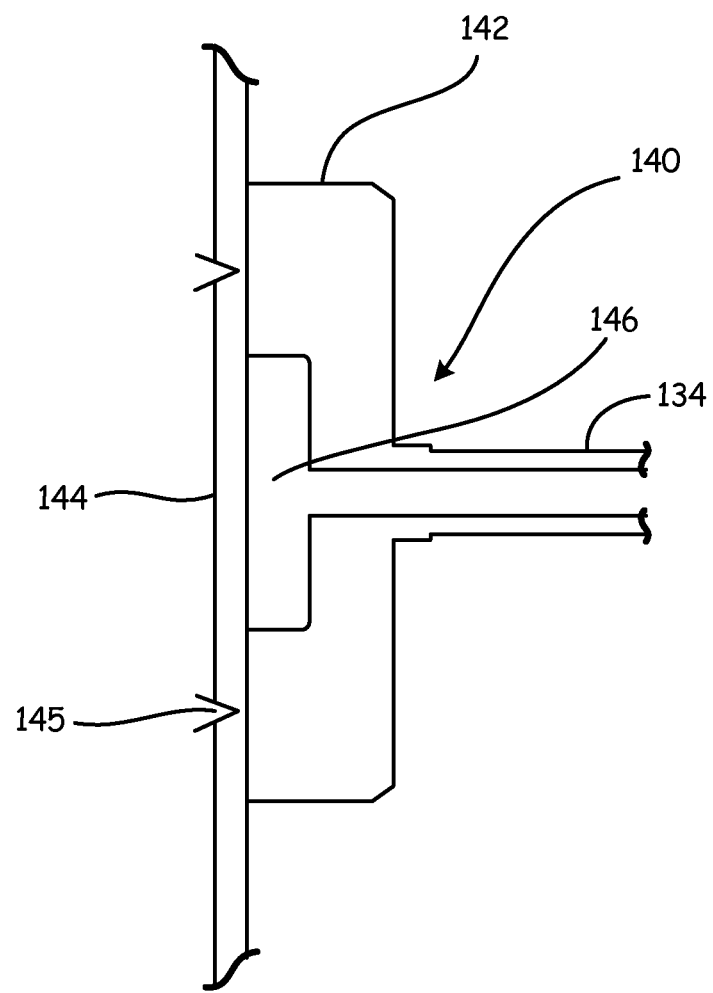
FIG. 2B is a partial cross-sectional view of a process-side connection of a remote seal system in accordance with another embodiment of the present invention.

FIG. 2B is a diagrammatic cross-sectional view of a process-side coupling of a remote seal system in accordance with another embodiment of the present invention. Remote seal system 140 includes a flange body 142 that is attached, such as via annular weld 145 to wall 144 of a single-use bioreactor bag. Accordingly, the embodiment illustrated with respect to FIG. 2B eliminates any seals and provides a simple connection for headspace and level measurements. Further, bag wall 144 functions to not only contain the bioreaction, but also to deflect in response to pressure therein such that the deflection of wall 144 causes movement of fluid within region 146, which ultimately causes fluid flow through tubing 134. Flange body 142 is generally formed of a radiation-sterilizable polymer. However, the selection of material for flange body 142 can also be tailored such that it is readily weldable or otherwise attachable to materials that are commonly used for single-use bioreactors.

FIG. 2C is a diagrammatic cross-sectional view of a process-side coupling of a polymeric remote seal system in accordance with another embodiment of the present invention. Process-side coupling 150 includes tubing connector 152 coupled to tubing 134. Tubing connector 152 is generally formed of a radiation-sterilizable polymer. Connector 152 includes one or more stepped portions 154, 156 that are configured to retain flexible tubing that is passed over the outside diameter of connector 152. In the embodiment shown in FIG. 2C, the flexible tubing that passes over stepped portions 154, 156 couples region 158 to the interior of the bioreactor. Process-side coupling 150 includes a small collapsible bellows structure 159 that is attached, for example via weld 161, to connector 152. Thus, bioreactor fluid pressure P acts upon surface 160 to collapse bellows 162 and thereby reduce the volume within region 164. This reduction in volume forces fluid therein through tubing 134, which fluid movement is detected as pressure by instrument 104.

Figure 2D:
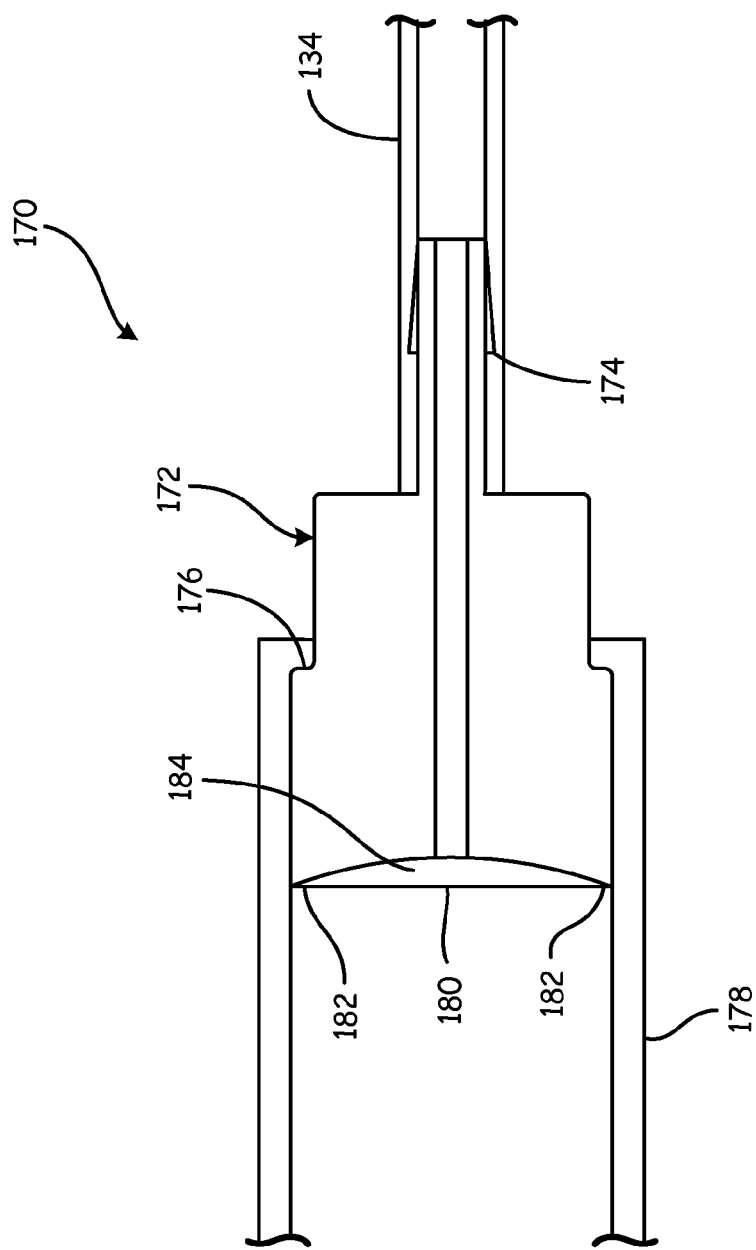
FIG. 2D is a partial cross-sectional view of a process-side connection of a remote seal system in accordance with another embodiment of the present invention.

FIG. 2D is a diagrammatic cross-sectional view of a process-side coupling of a polymeric remote seal system in accordance with another embodiment of the present invention. Coupling 170 includes tubing connector 172 that is, in one embodiment, formed of a radiation-sterilizable polymer. Connector 172 includes at least one stepped portion 174 that is configured to retain tubing 134 as tubing 134 is slipped over portion 174. Additionally, connector 172 includes another stepped portion 176 sized and configured to receive and retain tubing 178 which is coupled to a single-use bioreactor. Connector 172 includes a deflectable isolation diaphragm 180 attached, such as by thermal or ultrasonic welding, to connector 172 at location 182. Accordingly, pressure within tubing 178 acts upon diaphragm 180 to cause movement of diaphragm 180 which changes the volume within region 184 thereby causing fluid flow through tubing 134.

Figure 3A:
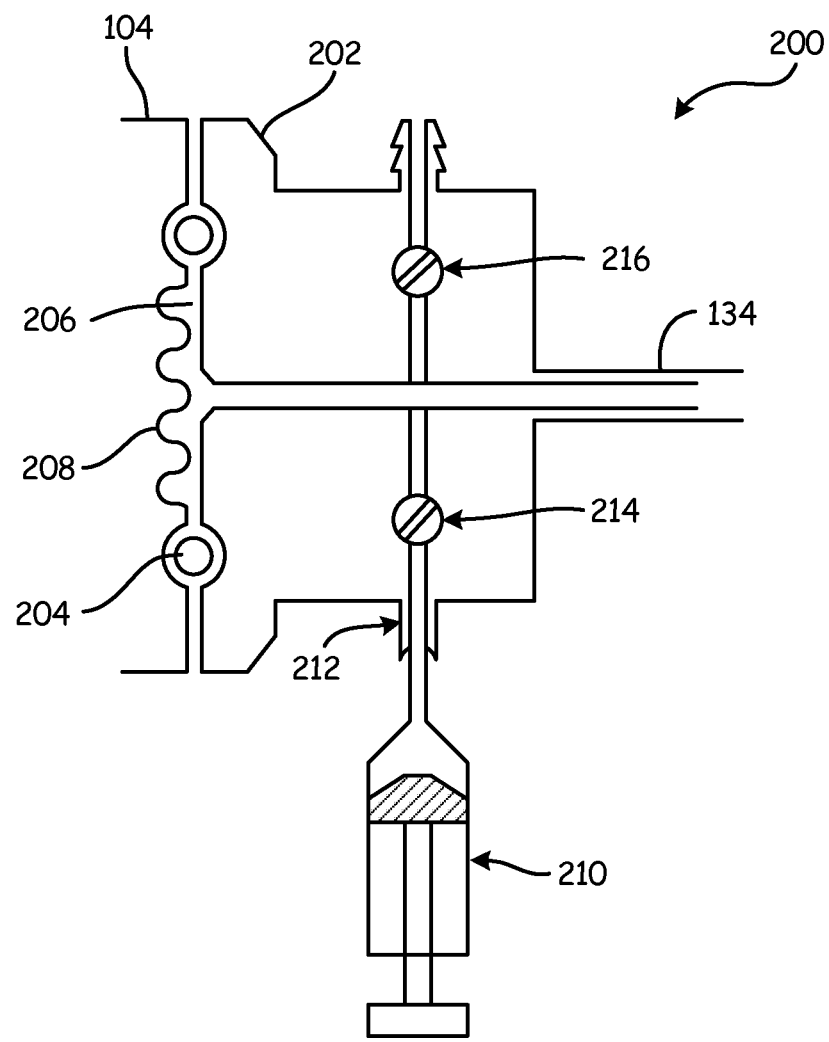
FIG. 3A is a diagrammatic view of an instrument-side connection of a polymeric remote seal system in accordance with an embodiment of the present invention.

FIG. 3A is a cross-sectional diagrammatic view of an instrument-side coupling of a polymeric remote seal system in accordance with an embodiment of the present invention. Coupling 200 includes flange 202 attached or otherwise coupled to instrument 104 via any suitable methods, such as clamping, bolts, or any combination thereof. A seal 204 is sandwiched between flange 202 and instrument 104 in order to create a fluid-tight chamber 206 therein. Chamber 206 is bounded, on one side, by deflectable isolation diaphragm 208 of instrument 104. Accordingly, deflection of diaphragm 208 will cause an associated deflection of a measuring diaphragm or structure of a pressure sensor within instrument 104 such that the pressure is detectable. Tubing 134 that is operably coupled to a single-use container such as bioreaction vessel is attached to flange 202. Flange 202 is, in one embodiment, formed of a radiation-sterilizable polymer. In the embodiment shown in FIG. 3A, the remote seal system is filled with a substantially incompressible fluid prior to use. Accordingly, a syringe, such as syringe 210 is inserted into flange 202 at port 212. Port 212 is valved, using tubing valve 214, while a diaphragm pump or other suitable device is operably coupled to flange body valve 216. The first step of filling the remote seal system with fluid is to evacuate air from the disposable process connection. Accordingly, the vacuum pump is engaged and valve 216 is opened in order to evacuate all of the air from the system. After the air is evacuated, valve 216 is closed and tubing valve 214 is opened. A predetermined volume of fill fluid is pushed into the remote seal system using syringe 210. Then, valve 214 is closed. At this point, the pressure measuring instrument can be zeroed and the system is ready for use. After being used, the disposable remote seal system can be removed, the refill assembly can be drained, and a new process connection can be installed for the next application.

Figure 3B:
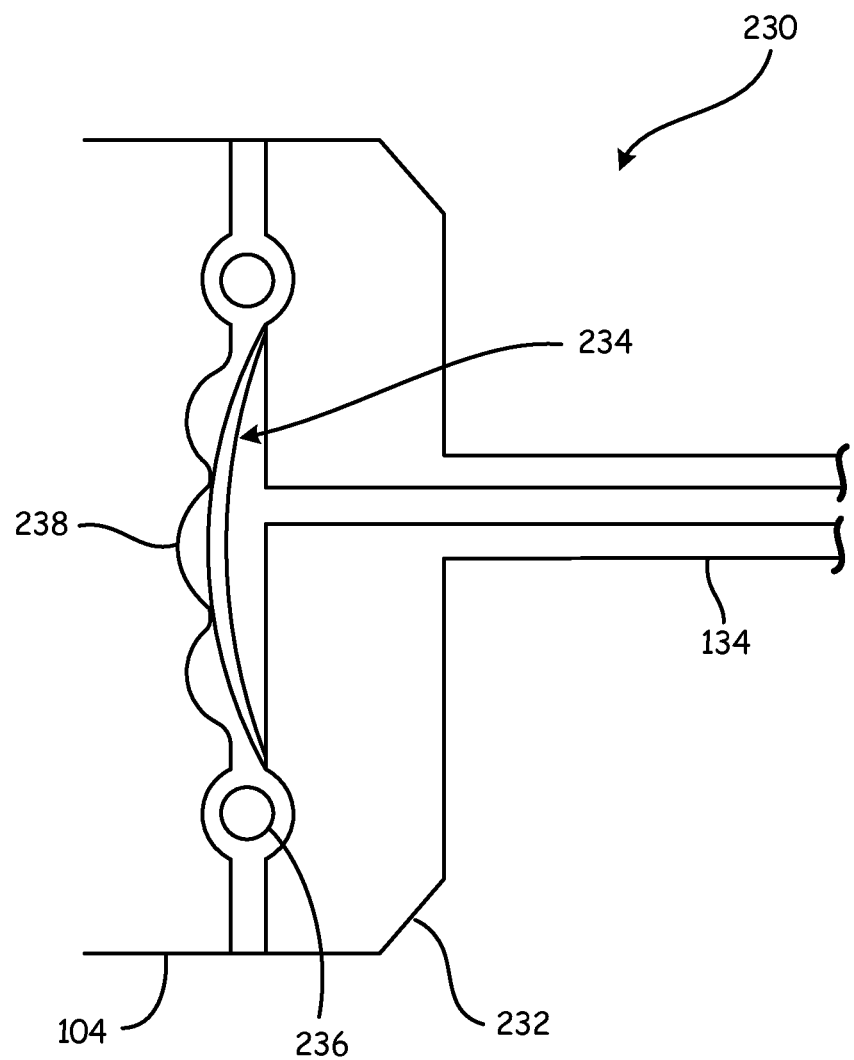
FIG. 3B is a diagrammatic view of an instrument-side connection of a polymeric remote seal system in accordance with another embodiment of the present invention.

FIG. 3B is a diagrammatic cross-sectional view of an instrument-side coupling of a polymeric remote seal system in accordance with another embodiment of the present invention. Coupling 230 includes a flange body 232 that, in one embodiment, is formed of a radiation-sterilizable polymer. Coupling 230 also includes a deformable polymeric membrane 234 operably coupled to flange body 232. Deformable polymeric membrane 234 is also, in one embodiment, formed of a radiation-sterilizable polymer. Membrane 234 may be coupled to flange body 232 in accordance with any suitable techniques. In one example, membrane 234 is welded to flange body 232. Thus, embodiments of the present invention can include a polymeric remote seal system that is pre-filled with fill fluid such that no filling is required by the user prior to use. Alternatively, embodiments of the present invention also include structures that allow a user thereof to fill the remote seal system with fill fluid prior to use. In use, flange body 232 is urged against instrument 104 to such an extent that seal 236 forms a fluid-tight connection. Accordingly, fluid pressure received through tubing 134 causes movement of deformable polymeric membrane 234, which causes similar movement of membrane 238 of instrument 104. Movement of membrane 238 conveys fluid pressure to a high accuracy pressure sensor within instrument 104 in order to accurately measure the pressure.

Figure 3C:
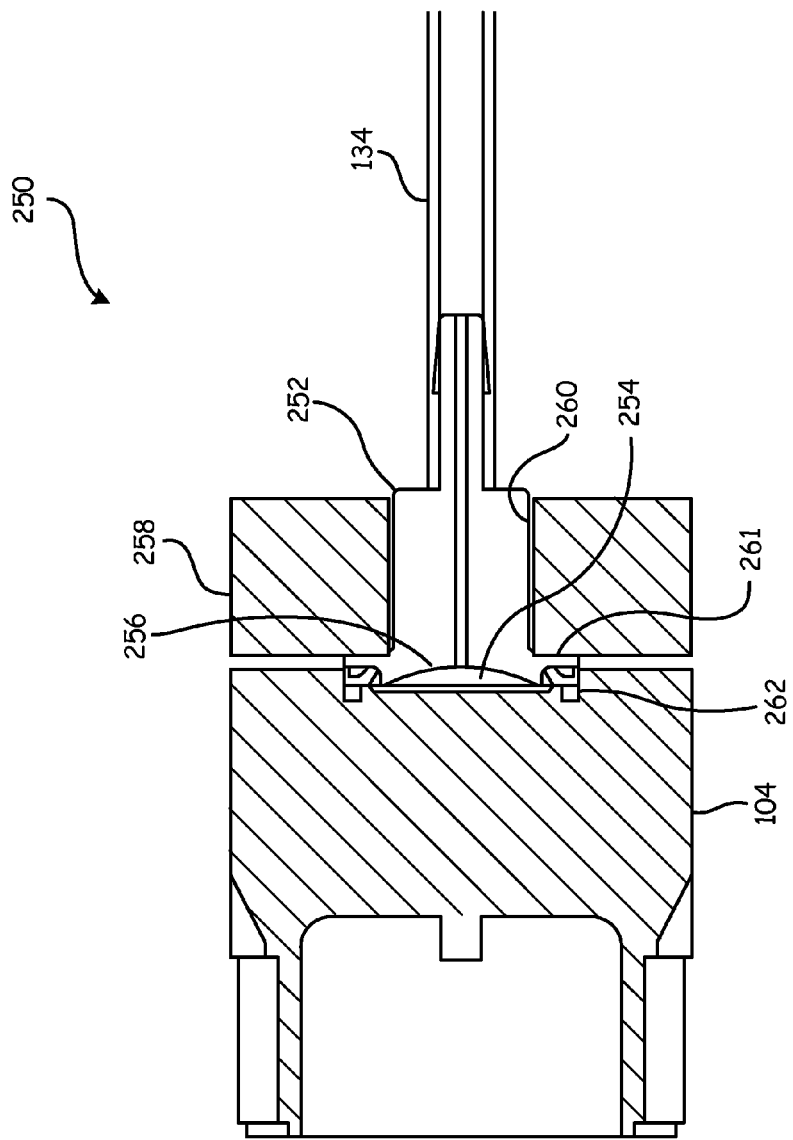
FIG. 3C is a diagrammatic view an instrument-side connection of a polymeric remote seal system in accordance with another embodiment of the present invention.

FIG. 3C is a diagrammatic cross-sectional view of an instrument-side coupling of a polymeric remote seal system in accordance with another embodiment of the present invention. Coupling 250 includes plastic body 252 coupled to tubing 134 such that bioreaction fluid pressure is conveyed through fill fluid within tubing 134 into chamber 254. A deformable polymeric diaphragm 256 is sealingly coupled to plastic body 232 such that fluid pressure within region 254 generates a deflection of plastic diaphragm 256. As set forth above, diaphragm 256 can be attached to flange 252 in a variety of ways, including ultrasonic or thermal welding. As indicated in FIG. 3C, flange 252 is urged against instrument 104 by instrument flange 258. Instrument flange 258 includes an aperture 260 that is sized to pass flange 252. However, flange 252 includes a shoulder 261 that receives the clamping pressure of instrument flange 258 and bears against seal 262. Thus, a fluid tight seal is generated when instrument flange 258 is urged against shoulder 261. One way in which is bias is accomplished is via mounting bolts, clamps, or the like. When so coupled, movement of diaphragm 256 generates an associated movement of the isolation diaphragm of instrument 104 which movement is then detected or otherwise measured by instrument 104 in order to provide a high quality pressure measurement.

Thus far, embodiments of the present invention have generally provided a direct fluidic coupling extending from a bioreactor all the way to a high-precision process fluid pressure measurement instrument. However, embodiments of the present invention can also leverage known remote seal systems in order to reduce the amount of material employed for the disposable portion of the remote seal system.

Figure 4:
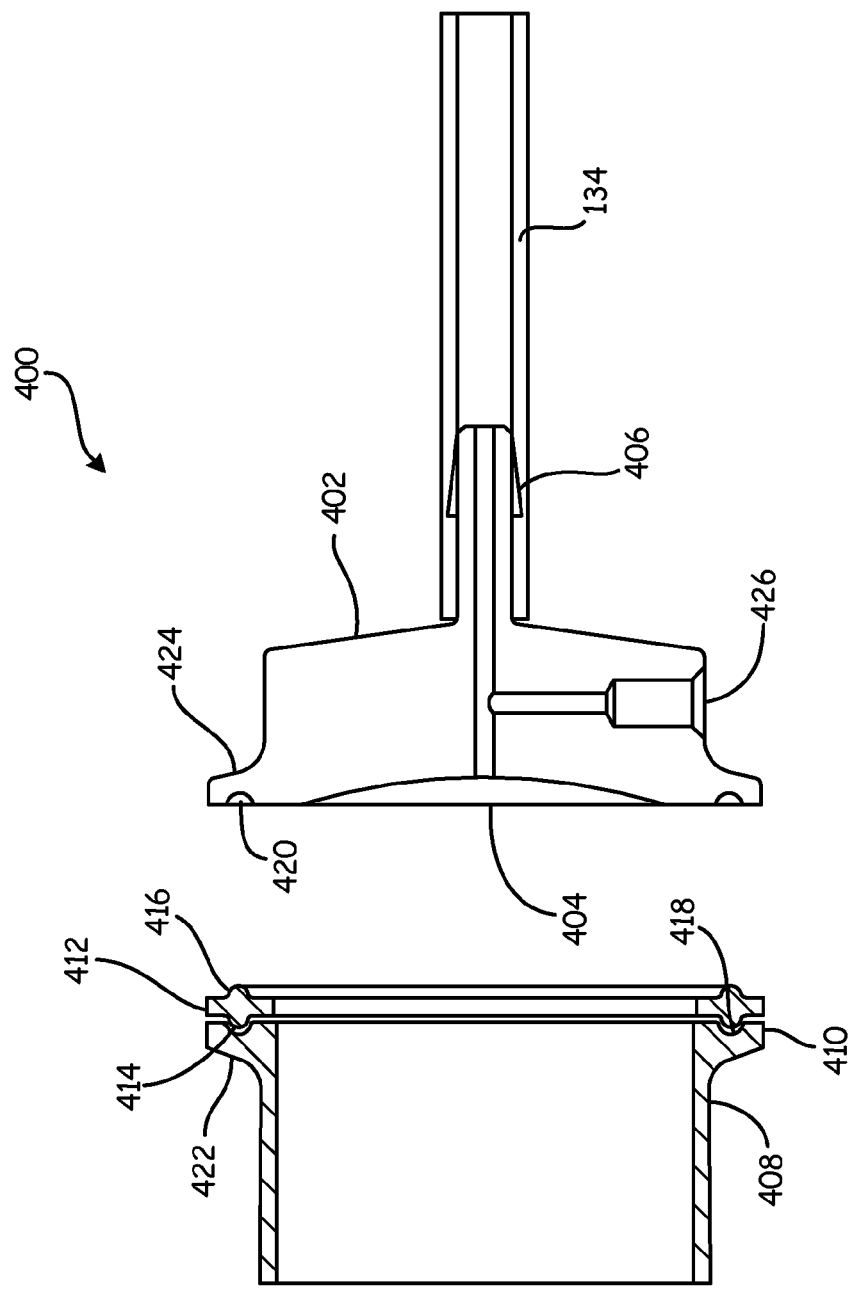
FIG. 4 is a diagrammatic cross-sectional view of a process-side coupling of a polymeric remote seal system in accordance with another embodiment of the present invention.

FIG. 4 is a diagrammatic cross-sectional view of a process-side coupling of a polymeric remote seal system in accordance with another embodiment of the present invention. Coupling 400 includes seal body 402 which, in one embodiment, is formed of a radiation-sterilizable polymer. Body 402 has a deflectable diaphragm 404 that is also, in one embodiment, formed of a radiation-sterilizable polymer. Diaphragm 404 is attached, via welding, or other suitable techniques, to body 402. Body 402 also includes a tubing connector 406 that is configured to receive tubing 134. A process coupler 408 is operably coupleable to a single-use bioreactor via any suitable techniques. Coupler 408 includes mounting region 410 that receives seal ring 412. Additionally, seal ring 412 has a pair of annular projections 414, 416 that extend into respective grooves 418, 420 in coupler 408 and body 402, respectively. Each of coupler 408 and body 402 have tapered portions 422, 424, respectively, such that a circumferential clamp encircling portions 422, 424 generates a force biasing coupler 408 and body 402 together. In this way, a fluid-tight seal is generated between coupler 408 and body 402.

Body 402 also, in one embodiment, includes fill port 426 that allows fill fluid to be introduced into body 402 prior to use. Accordingly, a single-use bioreactor can be provided with coupler 400 shown in FIG. 4 without any fluid present in the system. Moreover, such bioreactor/coupler system can be pre-sterilized using radiation prior to use. Then, the user need only introduce fill fluid into port 426 and couple the system to a process fluid pressure measurement instrument in order to monitor the pressure of the bioreaction. Further, those skilled in the art will recognize that fluid can be introduced into port 426 without destroying the sterilization since the fluid introduced in port 426 is on an opposite side of plastic diaphragm 404 from the sterilized interior of the bioreactor bag.

Figure 5:
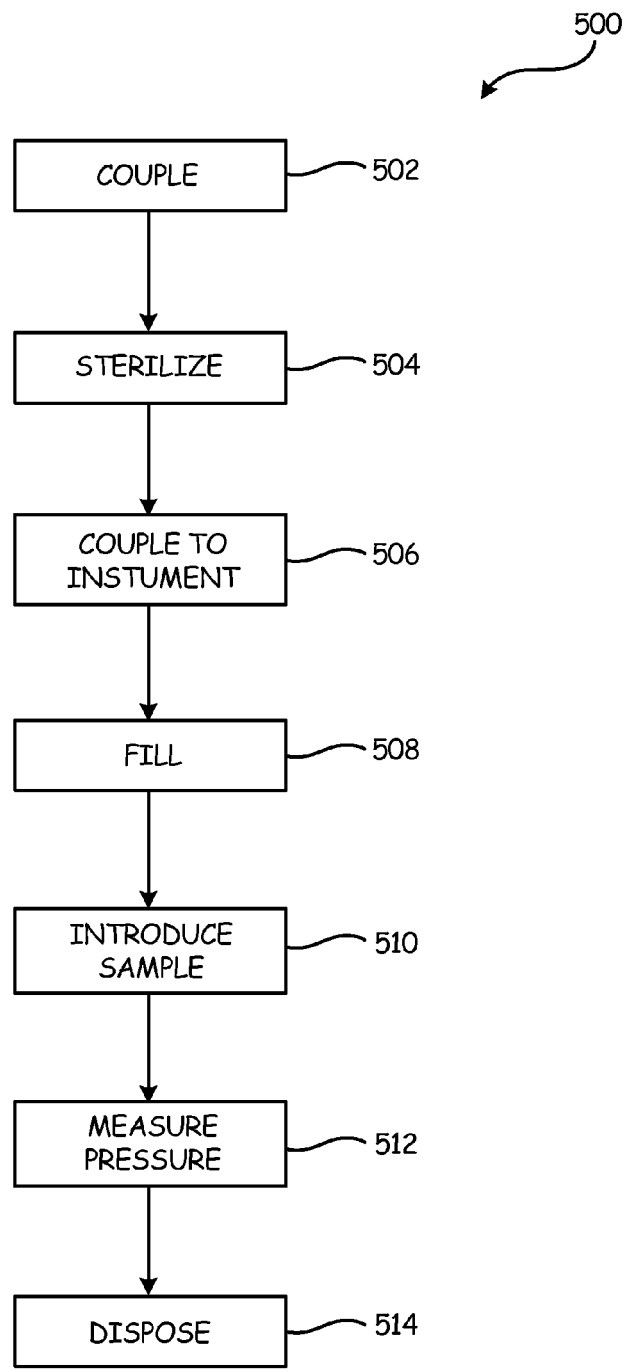
FIG. 5 is a flow diagram of a method of utilizing a polymeric remote seal system for a single-use bioreactor in accordance with an embodiment of the present invention.

FIG. 5 is a flow diagram of a method of using a polymeric remote seal system to monitor bioreaction pressure in accordance with an embodiment of the present invention. Method 500 begins at block 502 where the polymeric remote seal system is coupled to a bioreactor bag. Next, at block 504, the bioreactor bag/remote seal system is sterilized. In one embodiment, such sterilization employs a radiation process, such as a gamma radiation process. Next, at block 506, the sterilized bioreactor/remote seal system is operably coupled to a pressure measurement instrument, such as that illustrated with respect to FIG. 1. In embodiments where the remote seal system is pre-filled with fill fluid, method 500 may proceed directly to block 510 where the bioreaction sample is introduced into the bioreaction bag. However, in embodiments where fill fluid is not pre-filled in the remote seal system, block 508 is executed to provide the requisite fill fluid. As set forth above, one way in which the fill fluid can be introduced, is by first evacuating the remote seal system and then coupling the evacuated remote seal system to a source of fill fluid, such as via a syringe or other suitable instrument.

At block 512, the process measurement instrument is employed to measure the pressure within the bioreaction bag. This pressure may be measured continuously, periodically, intermittently, or in response to certain events. Finally, when the bioreaction process is complete, method 500 continues to block 514 where the polymeric remote seal system is decoupled from the instrument and discarded.

As set forth above, various embodiments of the present invention employ a polymeric remote seal system that is filled (either on-site, or pre-filled) with a fill fluid. The polymeric remote seal system can be made of plastic that can be sterilized. The seal system allows the use of an accurate, and relatively expensive, pressure measuring instrument. However, while the remote seal system is disposable, the pressure measuring instrument is reused. The polymeric remote seal system provides the user with a pre-sterilized connection to the process and a connection to the pressure measuring instrument. The polymeric remote seal system can be removed from the pressure measuring instrument and disposed of when the single-use bioreactor is disposed.

Both sides of the polymeric remote seal system (the process-side and the instrument-side) may use similar constructions. Both sides will typically have a polymeric membrane with a gas permeation-inhibiting layer that is bonded to a polymeric seal. Fluid pressure from the process connection is passed through the fluid-filled system to the pressure measuring instrument. The process-side connection generally includes a plastic body that has a membrane bonded thereto which connects with a bioreactor bag or vessel. The instrument-side connection also generally includes a polymeric body with a membrane bonded thereto that passes the pressure to the instrument. The system can be filled with a variety of pressure transmission media and uses either a fill screw or plastic-welded fill connection. Once the polymeric remote seal system has reached its end of service, the system can be decoupled from the instrument and disposed of along with the single-use bioreactor. A new fluid-filled polymeric remote seal system can then be attached to the instrument and connected to a new single-use bioreaction bag.

Embodiments of the present invention have, thus far, generally been described with respect to a polymeric remote seal system being used in conjunction with a bioreactor. However, embodiments of the present invention are practicable with any single-use container. Another example of a single use container is an intermediate bulk container or chemical tote.

Figure 6:
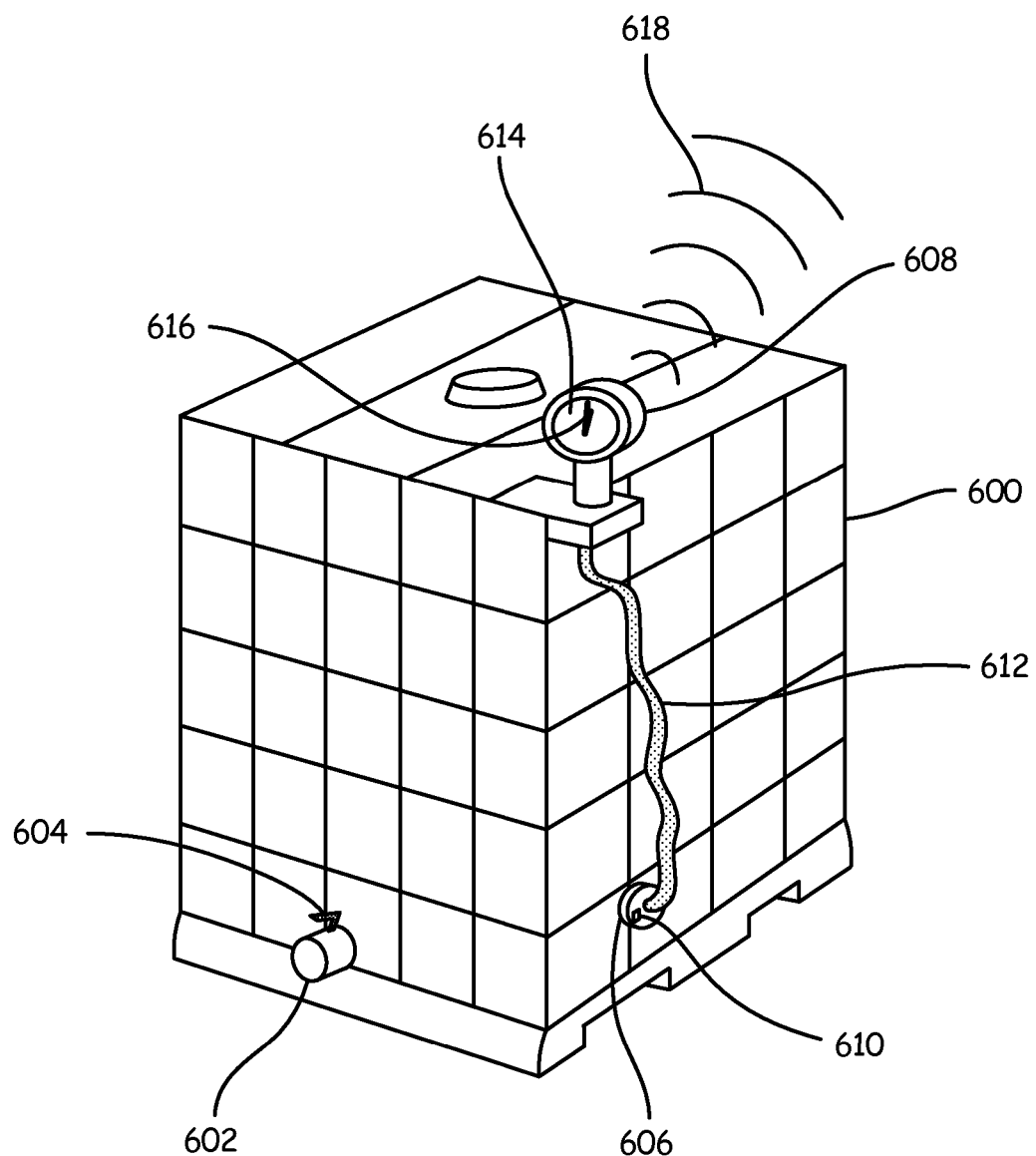
FIG. 6 is a diagrammatic view of a polymeric remote seal system being used on an intermediate bulk container in accordance with an embodiment of the present invention.

FIG. 6 is a diagrammatic view of a polymeric remote seal system being used on an intermediate bulk container (IBC) in accordance with an embodiment of the present invention. IBC 600 contains a quantity of liquid that may be dispensed from port 602 using valve 604. IBC 600 is coupled to polymeric remote seal system 606 such that the pressure of the liquid within IBC 600 acts against a polymeric isolation diaphragm of system 606 to fluidically convey the fluid pressure to measuring instrument 608. In one embodiment, polymeric remote seal system 606 includes optional temperature sensor 610 disposed in thermal contact with the contents of IBC 600. Temperature sensor 600 may be any suitable device that has an electrical characteristic that varies with temperature. Examples include, without limitation, thermocouples, resistance temperature devices (RTDs), thermistors, et cetera. Temperature sensor 610 is electrically coupled to measuring instrument 608 via two or more conductors illustrated diagrammatically in phantom at reference numeral 612. Accordingly, in some embodiments, measuring instrument is able to measure not only pressure, but temperature as well. Additionally, in one embodiment, measuring instrument 608 can be provided with an indication of liquid density of the contents of IBC 608. Once liquid density is known, measuring instrument 608 is able to provide an indication of liquid level within IBC 608 based on the measured pressure and the known density.

As shown in FIG. 6, measuring instrument 608 may, in some embodiments, provide a local indication relative to the contents of the single-use container to which it is coupled. In the example, a face 614 is provided with an indicator, such as a needle 616 that provides information relative to the contents. For example, when density is known, indicator 616 may provide a local indication of liquid level within IBC 600. Additionally, other variables, such as pressure and/or temperature of the contents may be displayed on face 614. Measuring instrument 608 also, in some embodiments, provides a digital indication of one or more variable to other devices wirelessly, as indicated at reference numeral 618.

Figure 7:
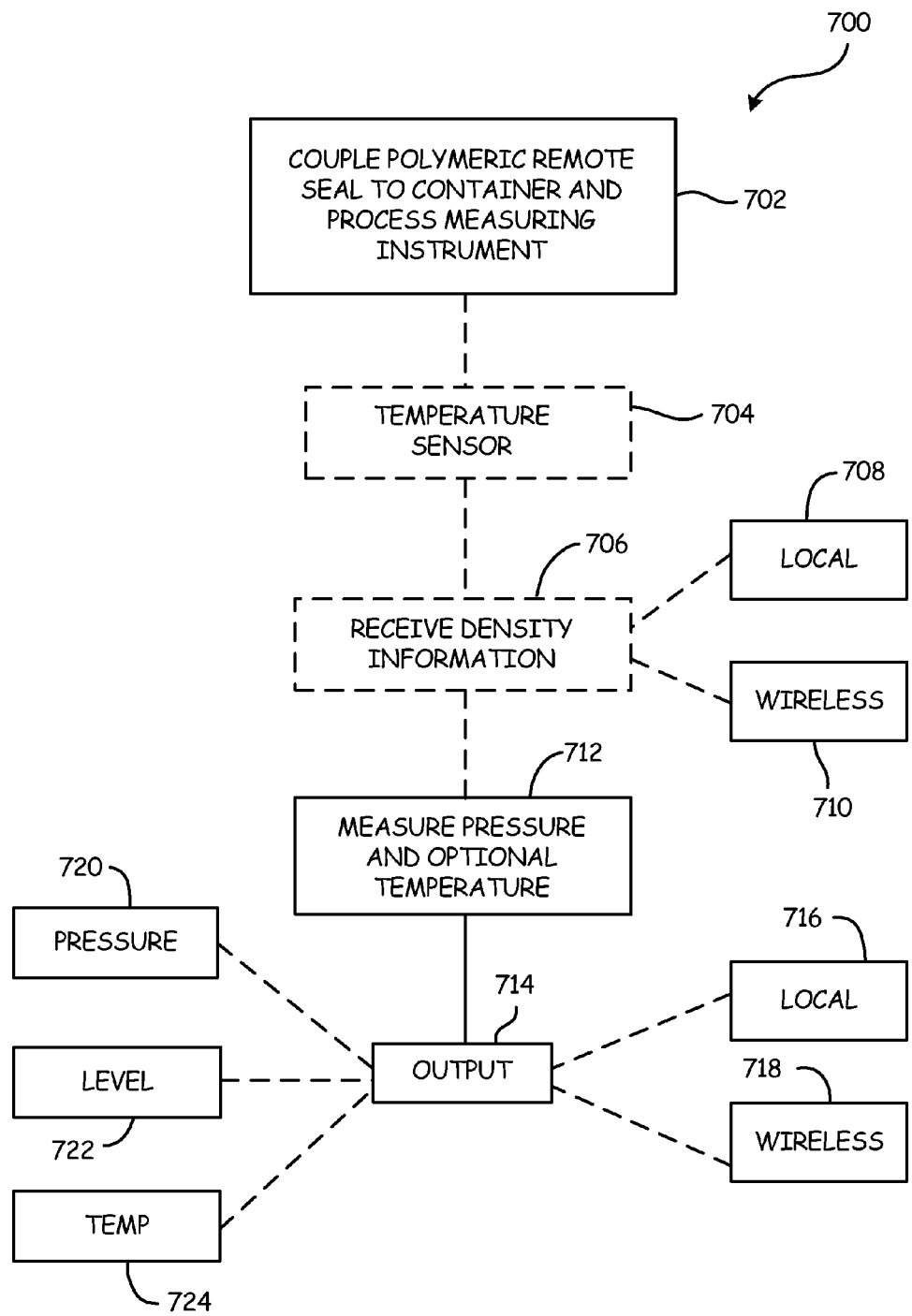
FIG. 7 is a method of using a polymeric remote seal system with an intermediate bulk container in accordance with an embodiment of the present invention.

FIG. 7 is a method of using a polymeric remote seal system with an intermediate bulk container in accordance with an embodiment of the present invention. Method 700 begins at block 702 where a polymeric remote seal system is used to couple a single-use container to a measuring instrument, such as instrument 608. In embodiments where the polymeric remote seal system includes a temperature sensor, the temperature sensor is electrically couple to the measuring instrument, as indicated at block 704. In embodiments where the measuring instrument can receive liquid density information, optional block 706 is executed. At block 706, the liquid density information is received by the measuring instrument. This provision of density information to the measuring instrument can be locally at the measuring device, as indicated at reference numeral 708 or via wireless communication with the measuring instrument, as indicated at reference numeral 710.

At block 712, the measuring instrument measures pressure and optionally temperature of the contents of the single-use container. At block 714, one or more outputs related to the measurements are provided. The output(s) can be provided locally, as indicated at reference numeral 716 and/or wirelessly as indicated at reference numeral 718. The output(s) provided at block 714 may be the measured pressure, a calculated level based on the pressure and known density, the temperature or any combination thereof. Additionally, the local output 716 and/or wireless output 718 can include alarm indications if, for example, the level is below a threshold or the temperature is above a threshold.

Embodiments described herein provide a convenient way to measure variables within a single-use container while still ensuring that high quality measurements are used. The polymeric remote seal system can be disposed of or left with the single-use container once the container is empty or replaced. This allows the use and re-use of an accurate, complex wireless measurement instrument with different single-use containers without cleaning as the instrument is isolated from the single-use container. When active monitoring of a single-use container is no longer required, the polymeric remote seal system can be disconnected from the measuring instrument or gauge and disposed or left with the single-use container. Then, a new polymeric remote seal system can be placed in the next single-use container and coupled to the same measuring instrument or gauge.

Although the present invention has been described with reference to preferred embodiments, workers skilled in the art will recognize that changes may be made in form and detail without departing from the spirit and scope of the invention.

What is claimed is:

1. A polymeric remote seal system for coupling a single-use container to a pressure measurement instrument, the system comprising:

a process-side coupling configured to couple to the single-use container, the process-side coupling being formed of a radiation sterilizable polymer and having a process-side deflectable diaphragm that is configured to deflect in response to pressure of the single-use container;

an instrument-side coupling configured to couple to the pressure measurement instrument, the instrument-side coupling being formed of a radiation sterilizable polymer and being configured to fluidically convey fluid pressure to an isolation diaphragm of the pressure measurement instrument; and tubing fluidically coupling the process-side coupling to the instrument-side coupling.

2. The polymeric remote seal system of claim 1, wherein the process-side coupling is configured to couple to the single-use container.

3. The polymeric remote seal system of claim 2, wherein the process-side coupling includes a flange body coupleable to the single-use container, wherein the flange body is welded to the process-side deflectable diaphragm.

4. The polymeric remote seal system of claim 2, wherein the process-side coupling includes a flange body that is coupled to a wall of the single-use container such that a portion of the single-use container wall forms the process-side deflectable diaphragm.

5. The polymeric remote seal system of claim 2, wherein the process-side coupling includes a tubing connector having at least one stepped portion configured to retain tubing coupled to the single-use container and wherein the process-side deflectable diaphragm is formed of a collapsible bellows structure disposed within the tubing connector.

6. The polymeric remote seal system of claim 2, wherein the process-side coupling includes a tubing connector having at least one stepped portion configured to retain tubing coupled to the single-use container and at least one stepped portion configured to retain the tubing coupling the process-side coupling with the instrument-side coupling.

7. The polymeric remote seal system of claim 1, wherein the instrument-side coupling includes a flange coupleable to the pressure measurement instrument, the flange having a plurality of ports therein, each port being valved by a respective valve.

8. The polymeric remote seal system of claim 7, and further comprising a seal disposed between the flange and the pressure measurement instrument.

9. The polymeric remote seal system of claim 8, wherein the system is configured to be filled with a fill fluid after coupling the flange to the pressure measurement instrument.

10. The polymeric remote seal system of claim 1, wherein the instrument-side coupling includes a flange and an instrument-side deflectable diaphragm coupled to the flange, wherein pressure from the single-use container causes the instrument-side deflectable diaphragm of the instrument-side coupling to bear against the isolation diaphragm of the pressure measurement instrument.

11. The polymeric remote seal system of claim 10, wherein the instrument-side deflectable diaphragm is welded to the flange.

12. The polymeric remote seal system of claim 10, wherein the polymeric remote seal system is pre-filled with fill fluid fluidically coupling the process-side coupling to the instrument-side coupling.

13. The polymeric remote seal system of claim 12, wherein the flange includes a shoulder configured to receive a clamping force to clamp the flange against the pressure measurement instrument.

14. The polymeric remote seal system of claim 13, and further comprising a seal disposed between the shoulder and the pressure measurement instrument.

15. A method of fluidically coupling pressure of a bioreactor to a pressure measurement instrument, the method comprising:

providing a polymeric remote seal system having a process-side connection and an instrument-side connection;

coupling the process-side connection to the bioreactor;

sterilizing the bioreactor and at least the process-side connection;

coupling the instrument-side connection to the pressure measurement instrument;

introducing a sample into the bioreactor; and using the pressure measurement instrument to measure pressure within the bioreactor.

16. The method of claim 15, and further comprising filling the polymeric remote seal system after coupling the instrument-side connection to the pressure measurement instrument.

17. The method of claim 15, and further comprising decoupling the polymeric remote seal system from the pressure measurement instrument and discarding the bioreactor and the polymeric remote seal system together.

18. A liquid measurement system comprising:

a polymeric remote seal system including:

a process-side coupling configured to couple to a single-use container, the process-side coupling being formed of a polymer and having a process-side deflectable diaphragm that is configured to deflect in response to pressure of the single-use container;

an instrument-side coupling fluidically coupled to the process-side coupling with tubing filled with an isolation fluid, the instrument-side coupling being configured to couple to a measuring instrument, the instrument-side coupling being formed of a polymer and being configured to fluidically convey fluid pressure to the measuring instrument; and a measuring instrument coupled to the polymeric remote seal system, the measuring instrument having an isolation diaphragm fluidically coupled to the instrument-side coupling of the polymeric remote seal system and configure to provide an output based on pressure conveyed by the instrument-side coupling.

19. The liquid measurement system of claim 18, wherein the polymeric remote seal system includes a temperature sensor coupled to the measuring instrument.

20. The liquid measurement system of claim 18, wherein the measuring instrument includes a local display.

21. The liquid measurement system of claim 20, wherein the measuring instrument provides a wireless output.

22. The liquid measurement system of claim 18, wherein the measuring instrument provides an indication of liquid level within the single-use container based on measured pressure and known liquid density.

* * * * *